United States Patent
Dodds et al.

(10) Patent No.: US 11,512,328 B2
(45) Date of Patent: Nov. 29, 2022

(54) METHODS AND SYSTEMS FOR 1-BUTANOL PRODUCTION

(71) Applicant: BIOCHEMINSIGHTS, INC., Malvern, PA (US)

(72) Inventors: David R. Dodds, Manlius, NY (US); William B. Armiger, Malvern, PA (US); Mattheos Koffas, Malvern, PA (US)

(73) Assignee: BIOCHEMINSIGHTS, INC., Malvern, PA (US)

( * ) Notice: Subject to any disclaimer, the term of this patent is extended or adjusted under 35 U.S.C. 154(b) by 0 days.

(21) Appl. No.: 16/911,458

(22) Filed: Jun. 25, 2020

(65) Prior Publication Data

US 2020/0325498 A1  Oct. 15, 2020

Related U.S. Application Data

(62) Division of application No. 15/552,647, filed as application No. PCT/US2016/019102 on Feb. 23, 2016, now Pat. No. 10,696,988.

(60) Provisional application No. 62/119,265, filed on Feb. 23, 2015.

(51) Int. Cl.
| | |
|---|---|
| *C12P 7/16* | (2006.01) |
| *C12N 9/02* | (2006.01) |
| *C12N 9/10* | (2006.01) |
| *C12N 9/88* | (2006.01) |
| *C12N 9/90* | (2006.01) |
| *C25B 15/02* | (2021.01) |
| *C25B 15/08* | (2006.01) |
| *C25B 3/25* | (2021.01) |
| *C25B 9/19* | (2021.01) |
| *C12M 1/00* | (2006.01) |
| *C12N 9/04* | (2006.01) |
| *C12N 15/52* | (2006.01) |

(52) U.S. Cl.
CPC .............. *C12P 7/16* (2013.01); *C12M 45/07* (2013.01); *C12N 9/001* (2013.01); *C12N 9/0006* (2013.01); *C12N 9/0008* (2013.01); *C12N 9/1029* (2013.01); *C12N 9/88* (2013.01); *C12N 9/90* (2013.01); *C12N 15/52* (2013.01); *C12Y 101/01001* (2013.01); *C12Y 101/01027* (2013.01); *C12Y 101/01157* (2013.01); *C12Y 102/0101* (2013.01); *C12Y 102/01046* (2013.01); *C12Y 102/01057* (2013.01); *C12Y 102/04001* (2013.01); *C12Y 103/01006* (2013.01); *C12Y 103/01038* (2013.01); *C12Y 203/01008* (2013.01); *C12Y 203/01009* (2013.01); *C12Y 203/01054* (2013.01); *C12Y 401/02043* (2013.01); *C12Y 503/01027* (2013.01); *C25B 3/25* (2021.01); *C25B 9/19* (2021.01); *C25B 15/02* (2013.01); *C25B 15/08* (2013.01); *Y02E 50/10* (2013.01)

(58) Field of Classification Search
None
See application file for complete search history.

(56) References Cited

U.S. PATENT DOCUMENTS

| | | | |
|---|---|---|---|
| 1,992,480 A | 2/1935 | Otto et al. | |
| 6,440,711 B1 | 8/2002 | Davé | |
| 10,696,988 B2 | 6/2020 | Dodds et al. | |
| 10,927,395 B2* | 2/2021 | Morrison | C12N 9/0059 |
| 2011/0177564 A1 | 7/2011 | Stephanopoulos | |
| 2012/0322078 A1* | 12/2012 | Mcbride | C12P 7/18 |
| | | | 435/6.18 |
| 2018/0037914 A1 | 2/2018 | Dodds et al. | |

FOREIGN PATENT DOCUMENTS

| | | |
|---|---|---|
| CN | 104126011 A | 10/2014 |
| CN | 105073997 A | 11/2015 |
| GB | 191504845 A | 3/1919 |
| WO | 2011/088425 | 7/2011 |
| WO | 2012/099934 | 7/2012 |
| WO | 2014/039767 | 3/2014 |
| WO | 2014/152434 | 9/2014 |
| WO | 2016137976 A1 | 9/2016 |

OTHER PUBLICATIONS

Kizer et al. Appl Environ Microbiol. May 2008;74(10):3229-41. (Year: 2008).*
Prather et al. CurrOpin Biotechnol. Oct. 2008;19(5):468-74. (Year: 2008).*
Dekishima et al., "Extending Carbon Chain Length of 1-Butanol Pathway for 1-Hexanol Synthesis from Glucose by Engineered *Escherichia coli*," Journal of the American Chemical Society, Aug. 3, 2011; vol. 133, issue 30, pp. 11399-11401.
Mitsui et al., "Formaldehyde Fixation Contributes to Detoxification for Growth of a Nonmethylotroph, Burkholderia cepacia TM1, on Vanillic Acid," Applied and Environmental Microbiology, Oct. 2003; vol. 69, No. 10, pp. 6128-6132.
H. Li et al., "Integrated Electromicrobial Conversion of CO2 to Higher Alcohols", Science, vol. 335, No. 6076, Mar. 30, 2012, pp. 1596-1596.
Atsumi S. et al., "Metabolic Engineering of *Escherichia coli* for 1-Butanol Production", Metabolic Engineering, Academic Press, US, vol. 10, No. 6, Nov. 1, 2008, pp. 305-311.

(Continued)

*Primary Examiner* — Christian L Fronda
(74) *Attorney, Agent, or Firm* — Greenberg Traurig, LLP; Fang Xie (57) ABSTRACT

A combination of an electrochemical device for delivering reducing equivalents to a cell, and engineered metabolic pathways within the cell capable of utilizing the electrochemically provided reducing equivalents is disclosed. Such a combination allows the production of commodity chemicals by fermentation to proceed with increased carbon efficiency.

15 Claims, 4 Drawing Sheets

(56) References Cited

OTHER PUBLICATIONS

Kizer et al., "Application of Functional Genomics to Pathway Optimization for Increased Isoprenoid Production", Appl Environ Microbial., vol. 74, pp. 3229-3241, May 2008.
Prather et al., "De novo biosynthetic pathways: rational design of microbial chemical factories", Current Opinion in Biotechnology, vol. 5, pp. 468-474, Oct. 19, 2008.
Si et al., "Utilizing an endogenous pathway for 1-butanol production in *Saccharomyces cerevisiae*", Metabolig Engineering, vol. 22, pp. 60-68, Epub Jan. 9, 2014.
International Preliminary Report on Patentability for corresponding International Application No. PCT/US2016/019102, dated Sep. 8, 2017.
Addo et al., "Methanol Production via Bioelectrocatalytic Reduction of Carbon Dioxide: Role of Carbonic Anhydrase in Improving Electrode Performance," Electrochemical and Solid State Letters, Feb. 15, 2011, vol. 14, No. 4, pp. E9-E13.
Aresta et al., "An integrated photocatalytic/enzymatic system for the reduction of CO2 to methanol in bioglycerol-water," Beilstein Journal of Organic Chemistry, 2014, vol. 10, pp. 2556-2565.
Aresta et al., "Catalysis for the Valorization of Exhaust Carbon: from CO2 to Chemicals, Materials, and Fuels. Technological Use of CO2," Chemical Reviews, Dec. 9, 2013, vol. 114, No. 3, pp. 1709-1742.
Aresta et al., "Utilisation of CO2 as a chemical feedstock: opportunities and challenges," Dalton Transactions, 2007, vol. 28, pp. 2975-2992.
Askaya et al., "Thermodynamic feasibility of enzymatic reduction of carbon dioxide to methanol," Applied Biochemistry and Biotechnology, Sep. 2010, vol. 162, No. 2, pp. 391-398.
Atalla, Moetaz L., "Recent Advances in Post-Combustion CO2 Capture Chemistry," American Chemical Society, May 3, 2012, vol. 1097. (Textbook).
Finn et al., "Molecular approaches to the electrochemical reduction of carbon dioxide," Chemical Communications, 2012, vol. 10., 1392-1399.
Hongo et al., "Application of Electro-energizing Method to L-Glutamic Acid Fermentation," Agricultural and Biological Chemistry, Oct. 1979, vol. 43, No. 1, pp. 2075-2081.

Kim et al., "Electron Flow Shift in Clostridiumacetobutylicum Fermentation by Electrochemically Introduced Reducing Equivalent," Biotechnology Letters, 1988, vol. 10, No. 2, pp. 123-128.
Obert et al., "Enzymatic Conversion of Carbon Dioxide to Methanol: Enhanced Methanol Production in Silica Sol-Gel Matrices," Journal of the American Society, Dec. 9, 1999, vol. 121, No. 51, pp. 12192-12193.
Park et al., "Utilization of electrically reduced neutral red by Actinobacillus succinogenes: physiological function of neutral red in membrane-driven fumarate reduction and energy conservation," Journal of Bacteriology, Apr. 1999, vol. 181, No. 8, pp. 2403-2410.
Qureshi et al., "Recent advances in ABE fermentation: hyper-butanol producing Clostridium beijerinckii BA101," Journal of Industrial Microbiology and Biotechnology, Nov. 2001, vol. 27, pp. 287-291.
Reda et al., "Reversible interconversion of carbon dioxide and formate by an electroactive enzyme," Proceedings of the National Academy of Sciences of the United States of America, Aug. 5, 2008, vol. 105, No. 31, pp. 10654-10658.
Russell et al., "The Electrochemical Reduction of Carbon Dioxide, Formic Acid, and Formaldehyde," Journal of The Electrochemical Society, 1977, vol. 124, No. 9, pp. 1329-1338.
Shin et al., "Evaluation of an electrochemical bioreactor system in the biotransformation of 6-bromo-2-tetralone to 6-bromo-2-tetralol," Applied Microbiology and Biotechnology, Nov. 2001, vol. 57, pp. 506-510.
Spinner et al., "Recent progress in the electrochemical conversion and utilization of CO2," Catalysis Science and Technology, 2012, vol. 2, pp. 19-28.
Tashiro et al., "Novel high-efficient butanol production from butyrate by non-growing Clostridium saccharoperbutylacetonicum N1-4 (ATCC 13564) with methyl viologen," Journal of Bioscience and Bioengineering, Sep. 2007, vol. 104, No. 3, pp. 238-240.
Xu et al., "Efficient Conversion of CO2 to Methanol Catalyzed by Three Dehydrogenases Co-encapsulated in an Alginate-Silica (ALG—SiO2) Hybrid Gel," Industrial and Engineering Chemistry Research, May 28, 2006, vol. 45, No. 12, pp. 4567-4573.
International Search Report in corresponding International Patent Application No. PCT/US16/19102, dated May 6, 2016.

* cited by examiner

METHODS AND SYSTEMS FOR 1-BUTANOL PRODUCTION

CROSS REFERENCE TO RELATED APPLICATIONS

This application is a divisional patent application of U.S. application Ser. No. 15/552,647, filed Aug. 22, 2017, which is a U.S. National Phase Application under 35 U.S.C. 371 of International Patent Application No PCT/US2016/019102, filed Feb. 23, 2016, which claims priority to and the benefit of U.S. Provisional Application No. 62/119,265 filed Feb. 23, 2015, the disclosure of each of which is incorporated herein by reference in its entirety.

FIELD

The disclosure relates generally to the use of a device, e.g., an electrochemical bioreactor (EBM), combined with one or more engineered metabolic pathways optionally expressed in a suitable host cell, for converting glucose or another fermentable carbon source to 1-butanol with a carbon efficiency exceeding that of carbon efficiencies in current fermentative processes for 1-butanol production.

BACKGROUND

The four-carbon compound 1-butanol has considerable value and utility as both a liquid fuel and as a commodity chemical. In particular, there is now increased interest in using biobutanol as a transport fuel. Various methods have been used to produce 1-butanol, including catalyzed reactions from the petrochemical feedstock propylene, catalyzed ethanol dimerization and ABE fermentation, all of which have significant disadvantages. New methods for butanol, in particular biobutanol production are urgently needed.

1-butanol is most commonly produced from the petrochemical feedstock propylene. In the presence of hydrogen and carbon monoxide, propylene undergoes hydroformylation using a cobalt or rhodium catalyst. The process requires temperatures of 100° C. to 200° C. and pressures up to 300 atm, and produces a mixture of approximately 88%

1-butanol and 12% iso-butanol. The reaction is illustrated below.

Ethanol, a two-carbon alcohol, can be dimerized using Geurbert chemistry to produce 1-butanol. This allows use of bio-ethanol, so that the 1-butanol produced is also bio-based. Geurbert chemistry has been known since the end of the 19th century, and patents employing that chemistry for the production of 1-butanol from ethanol date to the 1930s (U.S. Pat. No. 1,992,480). The process employs catalysts that perform a series of reactions (oxidation, aldol condensation, dehydration, and reduction) to give the higher alcohol plus a molecule of water. The reaction is illustrated below.

Thus, production of 1-butanol from propylene or ethanol via catalytic reactions requires expensive catalysts and/or harsh reaction conditions.

1-butanol can also be produced via fermentation using *Clostridium acetylbutylicum*. This fermentation process, called the Acetone-Butanol-Ethanol (ABE) process was patented in the early 20th century by Fernbach and Weizmann, and their processes were patented in 1912 and 1915 respectively; the Weizmann process (British Patent 4845, 6 Mar. 1919) eventually dominated the industrial production of acetone and butanol. The fermentation yields the three solvents, Acetone:1-Butanol:Ethanol, in an approximate ratio of 3:6:1. The tools of molecular biology have been applied, and a hyper-producing strain *Clostridium beijerincki* with yields of total solvents up to 165 g/L of 1-butanol has been published. (N. Qureshi, H. P. Blaschek, J. Ind. Microbiol. Biotechnol., 2001, 27, 287-291).

The metabolism of the *Clostridia* species used for the ABE fermentation is complex, passing through an acidogenic phase in which acetic and butyric acids are generated and excreted from the cell, followed by a solventogenic phase in which the acetic and butyric acids are taken back up by the cell and reduced to give ethanol, acetone, and butanol. Pathways have been engineered which allow the host organism to avoid this complex behavior, and produce 1-butanol from acetyl-CoA using the sequence of enzymes acetyl-CoA acetyltransferase (AtoB), 3-hydroxybutyryl-CoA dehydrogenase (Hdb), 3-hydroxybutyryl-CoA dehydratase (Crt), trans-enoyl-CoA reductase (Ter), and aldehyde/alcohol dehydrogenase (AdhE2) (Shota Atsumi et al., *Metabolic Engineering* 10 (2008) 305-311).

Regardless of the metabolism of the cell or the pathways present, balanced stoichiometry requires that the carbon efficiency is two-thirds, that is, of the 6 carbon atom present in the starting glucose ($C_6H_{12}O_6$) only 4 of then are present in the 1-butanol produced ($C_4H_{10}O$); the remaining 2 carbon atoms being lost as 2 molecules of carbon dioxide. As shown in the balanced equation below, this is the theoretical maximum carbon efficiency possible for the fermentation of glucose to 1-butanol.

$$C_6H_{12}O_6 \rightarrow C_4H_{10}O + 2CO_2 + H_2O \qquad \text{Equation I}$$

Biofuels now comprise approximately 10% of the total 130 billion gallons/year US automobile fuel market. By increasing the theoretical carbon efficiency of 1-butanol production from 66.6% to 100%, that is, if all the carbon in the starting glucose could be present in the 1-butanol product, this would increase raw material production yields by 50%. Advanced biofuels such as 1-butanol continue to penetrate the automobile fuel market, targeted at 36 billion gallons by 2022. Increased carbon efficiency could produce 36 billion gallons from the same amount of biomass and starch required to produce 24 billion gallons using today's process technology, making biofuels considerably more competitive.

Thus it is highly desirable to increase the carbon efficiency of the fermentation of glucose to 1-butanol.

Another issue illustrated by Equation I is the production of $CO_2$ which is lost carbon that is not transformed to the desired 1-butanol product. The loss of $CO_2$ from both biological and non-biological processes and the desirability of recovering the $CO_2$ has been recognized for many years (P. G. Russell et al., *J. Electrochem. Soc.* 1977, 124(9), 1329-1338). Reduction of $CO_2$ to methanol has been published (Robyn Obert et al., *J. Am. Chem. Soc.* 1999, 121, 12192-12193; Song-wei Xu et al., *Ind. Eng. Chem. Res.* 2006, 45, 4567-4573; Xiaoli Wang et al., *ACS Catal.* 2014, 4, 962-972; Torsten Reda et al., PNAS 2008 105(31), 10654-10658) and patented (U.S. Pat. No. 6,440,711 B1, Aug. 27, 2002) using electrochemical (Neil S. Spinner et al., *Catal. Sci. Technol.*, 2012, 2, 19-28), photochemical (Michele Aresta et al., Beilstein *J. Org. Chem.* 2014, 10, 2556-2565) and standard chemical methods.

Utilization of reducing equivalents produced electrochemically has been proposed for a form of artificial photosynthesis, in which the electrochemically supplied reducing equivalents replace those that would be normally provided by photosystem I. (In Recent Advances in Post-Combustion $CO_2$ Capture Chemistry; Attalla, M.; ACS Symposium Series; American Chemical Society: Washington, D.C., 2012). However, this proposal simply proceeded to generate starch, plus taking some of the pyruvate to ethanol and $CO_2$ in order to balance ATP requirements.

Improving carbon efficiency by the capture of $CO_2$ has been explored for from industrial waste gases (Michele Aresta, Angela Dibenedetto, Antonella Angelini, *Chem. Rev.*, 2014, 114 (3), 1709-1742; Michele Aresta, Angela Dibenedetto, *Dalton Trans.*, 2007, 2975-2992), through the reduction of $CO_2$ to formate, with the accompanying issues about gas transfer in liquids, and the need to form carbonic acid and bicarbonate from $CO_2$ prior to the reduction to formate.

The reduction of $CO_2$ to formate is energetically unfavorable (Colin Finn, Sorcha Schnittger, Lesley J. Yellowlees, Jason B. Love, *Chem. Commun.*, 2012, 48, 1392-1399; F. Suhan Baskaya, Xueyan Zhao, Michael C. Flickinger, Ping Wang, *Appl Biochem Biotechnol* (2010) 162: 391-398), and when coupled with the possible need to utilize carbonic anhydrase to first catalyze the conversion of $CO_2$ to carbonic acid to avoid the problem of gas transfer in liquids (Paul K. Addo, Robert L. Arechederra, Abdul Waheed, James D. Shoemaker, William S. Sly, Shelley D. Minteer, *Electrochemical and Solid-State Letters*, 14 (4) E9-E13 (2011)), the capture of $CO_2$ as a method for improving carbon efficiency appears unattractive in any system.

Thus, there is a need for an improved system and method for 1-butanol production that addresses all of the above issues, with decreased production cost (by, e.g., avoiding expensive catalysts), increased carbon efficiency and avoidance of $CO_2$ production.

SUMMARY

The present disclosure provides, in one aspect, a novel combination of metabolic engineering and electrochemical bioreactor technology for the production of 1-butanol in such an arrangement that prior art disadvantages are avoided. For example, use of metabolic engineering and bio-based production avoids the use of expensive catalysts and petrochemical feedstock that cannot be regenerated. Compared to ABE fermentation, production of carbon dioxide at the end of the glycolytic pathway is avoided by the presently disclosed systems and methods, with the carbon being captured as formate and recycled via enzymes of the RuMP pathway back to the beginning of the glycolytic pathway. In this manner, and by providing exogenous electrochemically generated reducing equivalents, the carbon efficiency of 1-butanol production from glucose may be increased from 66%, to 100%.

In one aspect, a system for 1-butanol production is provided, comprising: an electrochemical bioreactor module for providing reducing equivalents; a first engineered pathway for producing 1-butanol from acetyl-CoA; and a second engineered pathway for recovering carbon as formate from pyruvate, and converting the recovered formate to fructose-6-phosphate; wherein the reducing equivalents are provided to one or more redox enzymes in the first and/or second engineered pathways; and wherein optionally the first and second engineered pathways are present in an engineered cell.

In some embodiments, the first engineered pathway comprises acetyl-CoA acetyltransferase (AtoB, EC 2.3.1.9), 3-hydroxybutyryl-CoA dehydrogenase (Hbd, EC 1.1.1.157), 3-hydroxybutyryl-CoA dehydratase (Crt, EC 4.2.1.5), trans-enoyl-CoA reductase (Ter, EC 1.3.1.38) and aldehyde/alcohol dehydrogenase (AdhE2, EC 1.2.157/EC 1.1.1.1). The second engineered pathway can comprise pyruvate:formate lyase (Pfl, EC 2.3.1.54), formaldehyde dehydrogenase (Fld, EC 1.2.1.46), hexulose-6-phosphate synthase (HPS, EC 4.1.2.43), and 6-phospho-3-hexuloisomerase (HPI, EC 5.3.1.27).

In some embodiments, in the engineered cell, the endogenous pyruvate dehydrogenase (Pdh, EC 1.2.4.1) has been disabled, deleted or otherwise rendered non-functional. The endogenous fumarate reductase (FrdBC, EC 1.3.1.6), lactate dehydrogenase (Ldh, EC 1.1.1.27), acetaldehyde dehydrogenase (AdhE, EC 1.2.1.10) and/or acetyl-CoA-phosphate acetyltransferase (Pta, EC 2.3.1.8) may also have been disabled, deleted or otherwise rendered non-functional.

The one or more redox enzymes can be selected from formaldehyde dehydrogenase (Fld, EC 1.2.1.46), 3-hydroxybutyryl-CoA dehydrogenase (Hbd, EC 1.1.1.157), trans-enoyl-CoA reductase (Ter, EC 1.3.1.38) and aldehyde/alcohol dehydrogenase (AdhE2, EC 1.2.157/EC 1.1.1.1).

In another aspect, a system for 1-butanol production is provided, comprising: an electrochemical bioreactor module for providing reducing equivalents; an engineered cell for receiving and using the reducing equivalents to produce 1-butanol, wherein the engineered cell comprises exogenously introduced enzymes selected from pyruvate:formate lyase (Pfl, EC 2.3.1.54), formaldehyde dehydrogenase (Fld, EC 1.2.1.46), hexulose-6-phosphate synthase (HPS, EC 4.1.2.43), and 6-phospho-3-hexuloisomerase (HPI, EC 5.3.1.27), and wherein in the engineered cell the endogenous pyruvate dehydrogenase (Pdh, EC 1.2.4.1) has been disabled, deleted or otherwise rendered non-functional.

The engineered cell in some embodiments can further comprise exogenously introduced acetyl-CoA acetyltransferase (AtoB, EC 2.3.1.9), 3-hydroxybutyryl-CoA dehydrogenase (Hbd, EC 1.1.1.157), 3-hydroxybutyryl-CoA dehydratase (Crt, EC 4.2.1.5), trans-enoyl-CoA reductase (Ter, EC 1.3.1.38) and aldehyde/alcohol dehydrogenase (AdhE2, EC 1.2.157/EC 1.1.1.1). In certain embodiments, the engineered cell can have the endogenous fumarate reductase (FrdBC, EC 1.3.1.6), lactate dehydrogenase (Ldh, EC 1.1.1.27), acetaldehyde dehydrogenase (AdhE, EC 1.2.1.10) and/or acetyl-CoA-phosphate acetyltransferase (Pta, EC 2.3.1.8) disabled, deleted or otherwise rendered non-functional. In certain embodiments of the system, the reducing equivalents are transported by an electron transfer mediator (ETM).

In certain embodiments in connection with any system disclosed herein, the reducing equivalents are transported by an electron transfer mediator (ETM), selected from, e.g., one or more of Neutral Red, Methylene Blue, Methyl Viologen, quinone, NAD+ and NADP+.

The cell in some examples can be a bacterium or a fungus. The bacterium can be selected from *E. coli*, *Actinobacillus succinogenes*, *Bacillus subtilis*, *Clostridium acetylbutylicum* or another *Clostridium* species. The fungus can be selected from *Saccharomyces cerevisiae*, the Cargill CB1 yeast, a *Pichia* species or an *Aspergillus* species.

Also provided is method for producing 1-butanol, comprising providing any system disclosed herein in the presence of a carbon source. The carbon source in some embodiments is glucose.

DETAILED DESCRIPTION

Systems and methods are provided herein for the production of commodity, specialty, performance or fine chemicals such as 1-butonal by one or more redox enzymes which require the addition of reducing equivalents. The system allows operating conditions to be conveniently altered to achieve maximal electrochemical efficiencies for a given enzymatically mediated redox reaction or series of reactions. In some embodiments, the series of reactions are organized by way of one or more engineered metabolic pathways, in vivo or in vitro. In certain embodiments, an in vivo system, e.g., a host cell such as *E. coli*, *Clostridium acetylbutylicum* and *Saccharomyces cerevisiae*, can be used where the undesirable endogenous genes have been deleted or otherwise inactivated, and exogenous genes have been introduced to provide additional catalytic reactions. In some embodiments, one or more enzymes of the engineered metabolic pathways can be provided in an in vitro environment (e.g., cell-free system) via recombinant technology.

In one aspect, the present disclosure provides a novel combination of metabolic engineering and electrochemical bioreactor technology for the production of 1-butanol such that production of carbon dioxide is avoided. $CO_2$ is normally produced at the end of the glycolytic pathway that converts glucose into pyruvate. In some embodiments, the carbon can be captured as formate and recycled via engineered enzymes of the ribulose monophosphate (RuMP) pathway back to the beginning of the glycolytic pathway. In this manner, and by providing exogenous electrochemically generated reducing equivalents, the carbon efficiency of 1-butanol production from glucose may be increased from 66%, to 100%. Further, by producing formate rather than $CO_2$ at the end of the glycolytic pathway, the problems of having to capture $CO_2$ and then reduce it to formate for carbon recovery can be avoided.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

The articles "a" and "an" are used herein to refer to one or to more than one (i.e., at least one) of the grammatical object of the article. By way of example, "an element" means one element or more than one element.

"Electrochemical bioreactor module" (EBM) as used herein means a system that utilize a combination of redox reactions either to produce useful electrical energy, or use electrical energy to drive a combination of useful redox reactions. Exemplary EBM suitable for use in connection with the present disclosure includes those disclosed in PCT Publication No. WO2014039767 and PCT Application No. PCT/US2015/058560, both of which are incorporated herein by reference in their entirety. The general term "redox" reaction is short for oxidation-reduction reaction. A redox reaction is one which involves the transfer of electrons from one chemical species to another.

The electrons, which are balanced by protons, are termed "reducing equivalents" or "reducing power". The reducing equivalents are generally provided to the redox enzyme via a cofactor such as nicotinamide adenine dinucleotide (NAD), nicotinamide adenine dinucleotide phosphate (NADP), quinones, and flavin adenine dinucleotide (FAD).

As used herein, the term "electron transfer mediator" or "ETM" means a molecule capable of accepting one or more electrons itself, and then transferring electrons to another molecule, including the transfer of electrons to an enzyme molecule. A typical and well known ETM is Neutral Red, which is also used as a pH indicator. Other compounds that can function as an ETM include Methylene Blue, Methyl Viologen, and quinone. Most generally, and compound whose reduction potential is more negative than that of NAD+ can be used, and this includes a variety of compounds generally termed redox dyes. For example, in the situation previously described, the Neutral Red is acting as an electron transport mediator by facilitating the movement of electrons from the cathode to the NAD+ cofactor, thus facilitating the reduction of the NAD+ to produce NADH.

The term "electron transport mediator" or "ETM" can include molecules that facilitate the transfer of electrons to an enzyme molecule, thus in a broad sense cofactors (e.g., NADH, FMN, FAD, ferredoxin, etc.) may also be considered an electron transfer mediator. However, in some examples, the term "electron transport mediator" or ETM is meant to describe only those molecules which facilitate the transfer of electrons, but which are not otherwise generally considered to be the naturally occurring cofactors of redox enzyme systems, for example, NADH, FMN, FAD, ferredoxin and the like.

In the context of the present disclosure, ETMs are generally considered desirable for facilitating the transfer of electrons from the actual cathode surface to the cofactors of redox enzyme systems. However, the cofactors of redox enzyme systems can themselves be capable of accepting electrons directly from the surface of the cathode without mediation by an ETM molecule. Thus, in the general case, the use of an ETM is optional, although will be preferred in some embodiments of the present disclosure.

As used herein, a "redox enzyme" is an enzyme catalyzing a reaction that results in a change of chemical oxidation state of the molecule being acted upon, such molecule being termed the "substrate". In the course of the reaction, the substrate molecule accepts electrons via the redox enzyme to produce a molecule that is more chemically reduced than the substrate molecule. This reduced molecule is the "reduced product", or more simply, the "product". Exemplary products include commercially or industrially important products, such as succinic acid (reduced from, e.g., fumarate), methane (reduced from, e.g., $CO_2$), butanediol, ethanol, butanol, fatty acids and other alcohols. In one embodiment, 1-butanol is a desired product.

As used herein, "including," "comprising," "having," "containing," "involving," and variations thereof, are meant to encompass the items listed thereafter and equivalents thereof as well as additional items. "Consisting of" shall be understood as a close-ended relating to a limited range of elements or features. "Consisting essentially of" limits the scope to the specified elements or steps but does not exclude those that do not materially affect the basic and novel characteristics of the claimed invention.

Other terms used in the fields of recombinant nucleic acid technology, metabolic engineering, and electrochemistry as used herein will be generally understood by one of ordinary skill in the applicable arts.

Electrochemical Bioreactor Module

The desired increase in carbon efficiency of the fermentive production of 1-butanol requires the addition of hydrogen. Glucose is more highly oxidized than the 1-butanol, that is, glucose contains less hydrogen. Thus extra hydrogen must be added in order for all the carbon in the starting glucose to be transformed into the product 1-butanol, and prevention of carbon lost as $CO_2$. By providing hydrogen, all carbon present in the starting glucose can be transformed to the 1-butanol product with no loss of carbon as $CO_2$, as shown in the balanced equation below. It will be clear that by providing sufficient hydrogen, all of the carbon present in the glucose starting material can be carried into the desired 1-butanol product, and the yield of 1-butanol can be increased by 50% as shown in Equation II.

$$C_6H_{12}O_6 + 6H_2 \rightarrow 1.5C_4H_{10}O + 4.5H_2O \quad \text{Equation II}$$

It is possible to feed hydrogen gas to a fermentation process, but this requires hydrogen gas being present in the headspace of the fermentation vessel and the need for special construction to handle flammable and explosive gases. Adding gas to a fermentation also requires the use of significant power for agitation to enhance the transfer of individual molecules of the gas from the bulk gas phase, through the bulk liquid phase, to make contact with the cells in the fermentation broth. Thus it is desirable to avoid the use of hydrogen gas while still providing the reducing power of the hydrogen.

Rather than supplying hydrogen gas, according to one aspect of the present disclosure, the necessary reducing equivalents can be provided to a fermentation by electrochemical methods.

Reduced electron shuttles can transfer electrons to several distinct electron-withdrawing compounds, such as azo dyes, polyhalogenated compounds, nitroaromatics and oxidized metalloids. Van der Zee and Cervantes have reviewed the results of reductive biotransformation process catalyzed by electron shuttles (Van der Zee et al. *Biotechnology Advances* 27: 265-277, 2009). In order for electrochemical bioreactors to become commercially viable a change in the hardware design and processes design of the conventional systems must take place in order to improve yield and efficiencies to practical levels.

Further, while others have previously recognized the desirability of providing external electrons to biological systems, the methods revealed for accomplishing this require the anode to be contained in a manner that will prevent it from undergoing undesired reactions with the bulk biological system. Thus, some physical arrangement must be made to provide electron transfer to the anode, while keeping the anode physically separate from the fermentation broth (in the case of whole cells) or a buffer system (in the case of isolated enzymes in aqueous medium), and this is done with a variety of membranes, salt bridges or other physical means. Simplifying the design of the electrochemical cell relative to previously revealed designs, and further, designing a cell for use in a continuous, flow-through system (such as a loop running through a large fermentation vessel or chemical reactor) is desirable. It is even more desirable to arrange the electrochemical cell in a manner that utilizes a simple half-reaction at the anode, and that operates in a manner to avoid the use of salt-bridges for connectivity of the anode and cathode chambers, and mitigates membrane fouling when a membrane is used to separate the anode and cathode chambers.

The above advantages are achieved by those disclosed in PCT Publication No. WO2014039767 and PCT Application No. PCT/US2015/058560.

In some embodiments, the present disclosure employs an "Electrochemical Bioreactor Module" (EBM) previously described in PCT Publication No. WO2014039767 and PCT Application No. PCT/US2015/058560, both of which are incorporated herein by reference in their entirety. The EBM most generally comprises an electrochemical cell with an anode contained in an anode chamber, a cathode contained in a cathode chamber, and a proton permeable membrane separating the two chambers.

Figure 1:
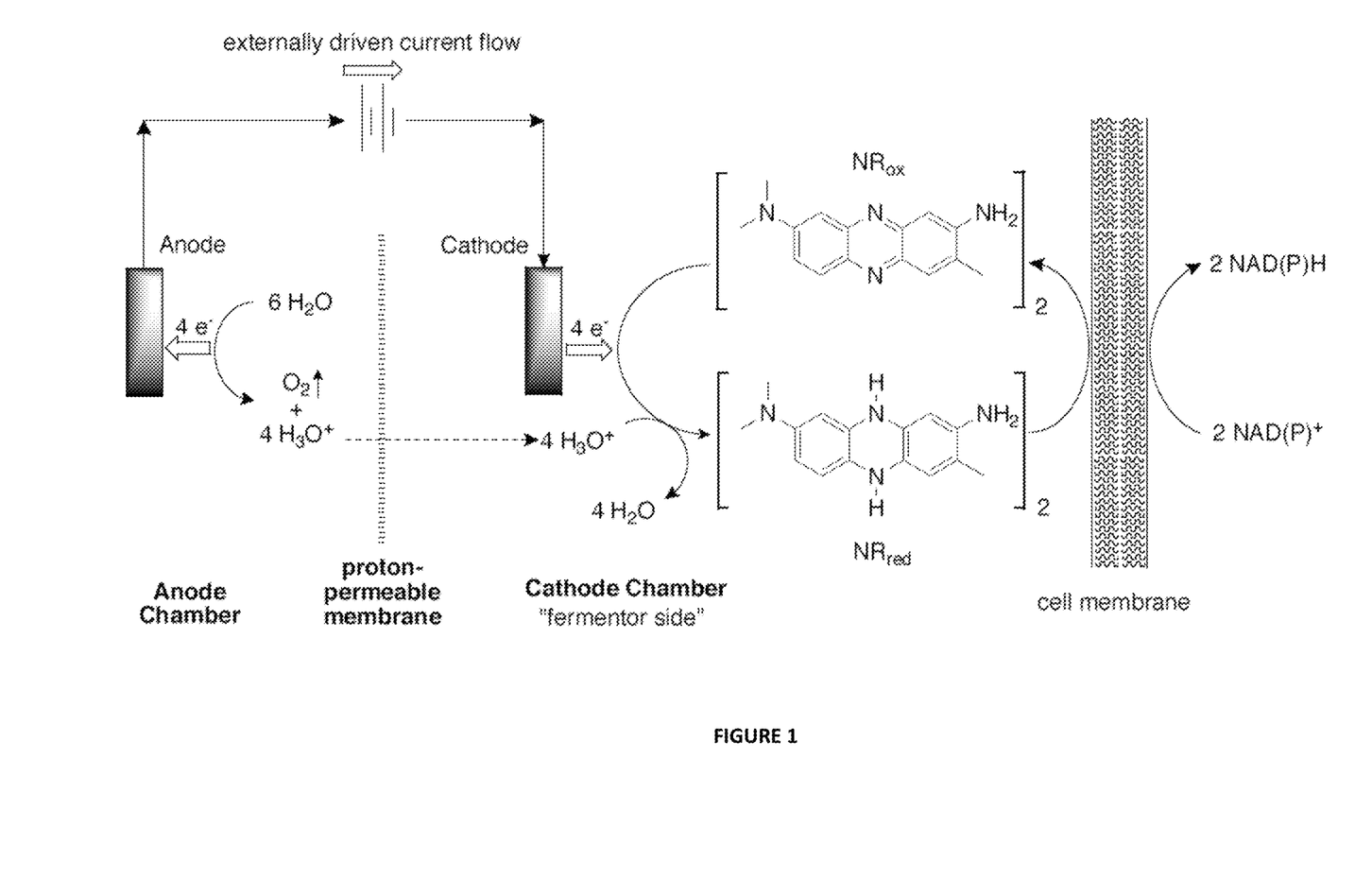
FIG. 1 illustrates the overall electrochemistry and general arrangement of the electrochemical cell. Neutral Red is shown as an exemplary electron transport mediator between the cathode and the redox cofactor NAD(P)+.

FIG. 1 illustrates the overall electrochemistry and general arrangement of the electrochemical cell. Neutral Red is shown as an exemplary electron transport mediator between the cathode and the redox cofactor NAD(P)+. For clarity, the stoichiometry shows a 4-electron transfer (2×2-electrons) to avoid fractional mols of $O_2$. For each pair of electrons provided by the electrochemical cell, one NAD(P)+ is reduced to one NAD(P)H and one water molecule is consumed. In this process, 1 molecule of $O_2$ generated for every 2 molecules of reduced NAD(P)H formed. It should be noted that the cell membrane in FIG. 1 is optional and only applicable when a host cell is used. Where in vitro or cell-free systems are used, the cell membrane can be absent.

In some embodiments, the EBM can include a proton permeable membrane that separates the anode and cathode chamber. The proton permeable membrane can be, in one embodiment, a modified Nafion® membrane which allows protons (as hydronium ions, $H_3O^+$) to travel across it. The proton permeable membrane may support or contain a catalyst on the anode side, for the production of oxygen gas.

The EBM further comprises an electrochemical cell with integrated instrumentation, that instrumentation comprising anode side oxygen collection system, cathode side gas collection system, flow rate control system, temperature measurement and control system, voltage and current measurement and regulation systems, pH measurement system, dissolved oxygen (DO) measurement system, conductivity measurement system, metabolic activity (fluorescence) measurement systems. Such an integrated system allows the following actions which are of great utility: electron and proton transfer regulation and optimization, microbial side product minimization, $H_2$ gas elimination or minimization, desired product optimization, distilled water (DI) water purity analysis, complete mass balance analysis, flow rate control, temperature control.

In the present disclosure, the anode may be any convenient design that allows useful current densities. Most typically, the anode will be a titanium substrate coated with platinum.

The anode chamber may be any convenient design that allows the input, recirculation, and temperature control of deionized water while simultaneously allowing the output, and optionally the collection, of gas generated at the anode surface, i.e. oxygen.

In use, the anode chamber can be filled with deionized water, and a sufficient voltage is applied to cause the electrolytic cleavage of water. This results in the formation of oxygen gas in the anode chamber, and this may be released to the atmosphere or captured for other use. The hydronium ions ($H_3O^+$) concomitantly produced migrate along the electric gradient and pass through the membrane separating the anode and cathode chamber. This causes a physical flux of water from the anode chamber into the cathode chamber.

Engineered Metabolic Pathways

In the present disclosure, the combination of a first engineered metabolic pathway for the production of 1 mol of 1-butanol from 2 mols of acetyl-CoA, and a second engineered metabolic pathway for transforming pyruvate into formate, then into formaldehyde and subsequently into fructose-6-phosphate, together optionally provided within a suitable host cell can be used to produce 1-butanol in a carbon-efficient manner. In various embodiments, an electrochemical bioreactor is used to provide exogenous, electrochemically generated reducing equivalents to the host cell. This allows the production of 1-butanol from glucose with 100% carbon efficiency.

Figure 2:
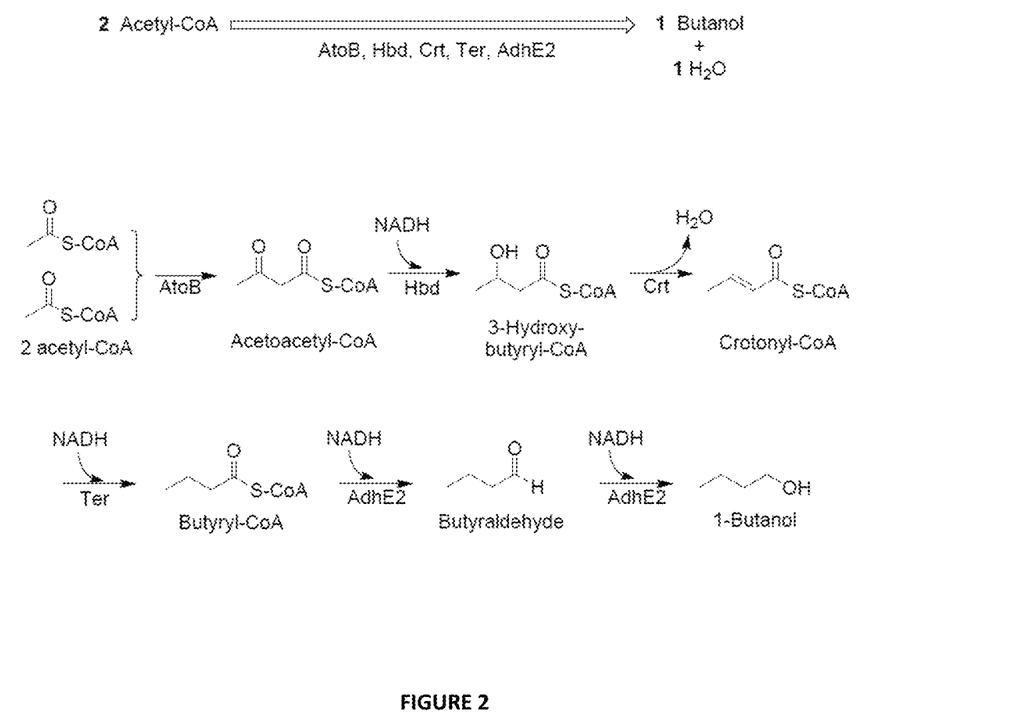
FIG. 2 illustrates the engineered metabolic pathway for the production of 1-butanol from acetyl-CoA using the enzymes AtoB, Hdb, Crt, Ter and AdhE2.

FIG. 2 illustrates the first engineered metabolic pathway for the production of 1-butanol from acetyl-CoA using the enzymes AtoB, Hdb, Crt, Ter and AdhE2, in which:
AtoB=acetyl-CoA acetyltransferase (EC 2.3.1.9)
Hbd=3-hydroxybutyryl-CoA dehydrogenase (EC 1.1.1.157)
Crt=3-hydroxybutyryl-CoA dehydratase (EC 4.2.1.5)
Ter=trans-enoyl-CoA reductase (EC 1.3.1.38)
AdhE2=aldehyde/alcohol dehydrogenase (EC 1.2.157/EC 1.1.1.1)
The various enzymes involved in the first engineered pathway are disclosed in Atsumi et al., *Metabolic Engineering* 10 (2008) 305-311, which is incorporated herein by reference.

In some embodiments, electrochemically generated, external reducing equivalents can be provided by the EBM disclosed herein to the redox enzymes in the first engineered metabolic pathway, such as Hbd, Ter and/or AdhE2. The reducing equivalents can be provided via one or more electron transfer mediators such as Neutral Red, Methylene Blue, Methyl Viologen, quinone, NAD + and/or NADP+.

Figure 3:
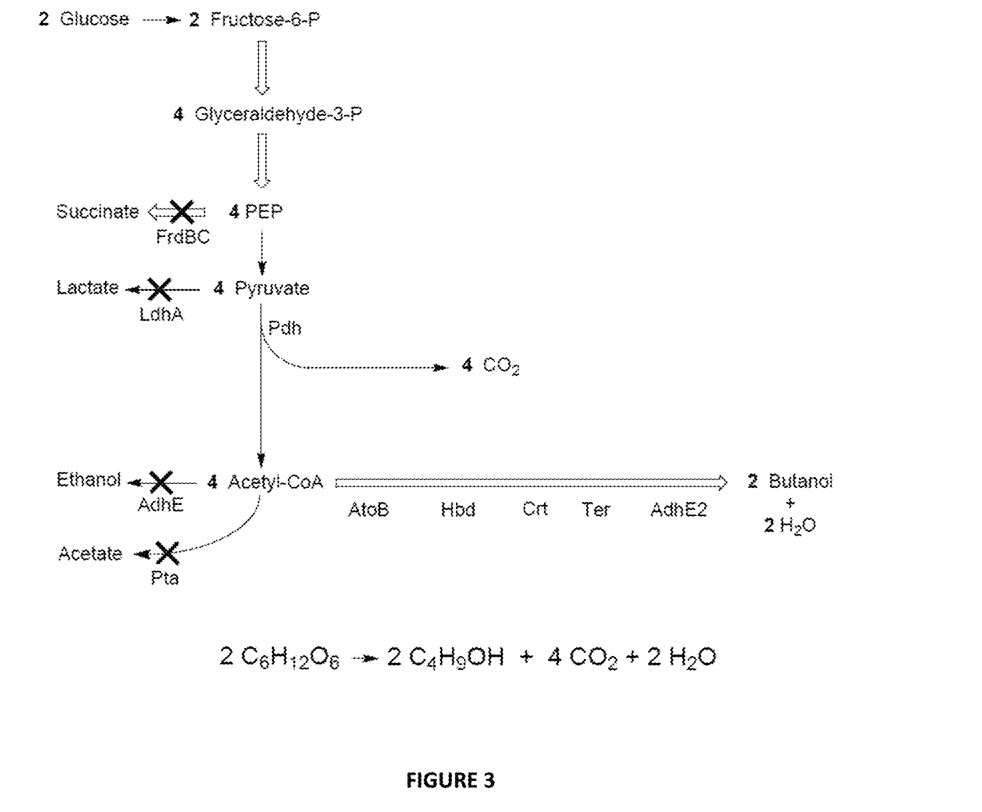
FIG. 3 illustrates the use of the engineered pathway in a host cell which the enzymes for the production of succinate, lactate, acetate, and ethanol, have been deleted or inactivated thus forcing all carbon to proceed from glucose to pyruvate. Pyruvate then proceeds to acetyl-CoA via pyruvate dehydrogenase (Pdh) with concomitant $CO_2$ production.

FIG. 3 illustrates the use of the engineered pathway within a host cell (e.g., *E. coli*) in which the endogenous enzymes for the production of succinate, lactate, acetate, and ethanol, have been deleted or inactivated thus forcing all carbon to proceed from glucose to pyruvate. Pyruvate then proceeds to acetyl-CoA via pyruvate dehydrogenase (Pdh) with concomitant $CO_2$ production. The bold numbers indicate molar equivalents of each compound in the pathway. In FIG. 3:
Pdh=pyruvate dehydrogenase (EC 1.2.4.1)

Inactivated or Deleted Enzymes

FrdBC=fumarate reductase (EC 1.3.1.6)
LdhA=lactate dehydrogenase (EC 1.1.1.27)
AdhE=alcetaldehyde dehydrogenase (EC 1.2.1.10)
Pta=acetyl-CoA-phosphate acetyltransferase (EC 2.3.1.8)

Butanol Pathway Enzymes

AtoB=acetyl-CoA acetyltransferase (EC 2.3.1.9)
Hbd=3-hydroxybutyryl-CoA dehydrogenase (EC 1.1.1.157)
Crt=3-hydroxybutyryl-CoA dehydratase (EC 4.2.1.5)
Ter=trans-enoyl-CoA reductase (EC 1.3.1.38)
AdhE2=aldehyde/alcohol dehydrogenase (EC 1.2.157/EC 1.1.1.1)

Engineered metabolic pathways that re-arrange the intracellular metabolism to generate increased amounts of NADH or NADPH reducing equivalents at the expense of decreasing the amount of ATP that is generated by the cell was previously disclosed (Peters et al., WO2008/293101). However, using that method it is not possible to alter the stoichiometry dictated by Equation I for 1-butanol production from glucose, and not possible to avoid the production of $CO_2$.

Carbon is lost as $CO_2$ at the end of the glycolytic pathway where the enzyme complex pyruvate dehydrogenase cleaves one molecule of pyruvate to one molecule of acetyl-CoA and one molecule of $CO_2$, generating one NADH reducing equivalent in the process. In some embodiments, the enzyme pyruvate:formate lyase (Pfl) can replace the pyruvate dehydrogenase complex at the end of the glycolytic pathway. The Pfl enzyme takes one molecule of pyruvate to one molecule of acetyl-CoA and one molecule of formate; no reducing equivalents are generated in this process. By preventing the carbon that is released by formation of acetyl-CoA from pyruvate from becoming $CO_2$, but keeping it as formate which remains as an ionic species in solution, the problems of having to capture $CO_2$ for carbon recovery can be avoided.

In some embodiments, the pyruvate:formate lyase disclosed by San et al., U.S. Pat. No. 7,709,261, incorporated herein by reference in its entirety, can be used in connection with the present disclosure. It should be noted that the formate generated by the pyruvate:formate lyase in U.S. Pat. No. 7,709,261 was then used to generate NADH with the formate being oxidized to $CO_2$ which was then lost. Thus, no carbon capture occurred.

In some embodiments, a second engineered pathway can be provided to capture the lost carbon. For example, the endogenous formate dehydrogenase can be replaced with engineered pyruvate:formate lyase, and the carbon captured in the form of formate can be recycled back into the glycolytic pathway. In some embodiments, the formate is first reduced to formaldehyde via the enzyme formaldehyde dehydrogenase (Fld), and this is taken further using enzymes of the Ribulose monophosphate (RuMP) pathway. In this pathway, one formaldehyde molecule is condensed with one ribulose-5-phosphate molecule by the enzyme 3-hexulose-6-phosphate synthase (HPS) to produce one molecule of 3-hexulose-6-phosphate. This is isomerized via the enzyme 6-phospho-3-hexuloisomerase (PHI) to give fructose-6-phosphate, which re-enters the glycolytic pathway, and produces acetyl-CoA and formate, thus repeating the cycle and preventing loss of carbon. Marrs et al., WO2010/104938 A1 discloses ethanol production where acetyl-CoA is reduced to acetaldehyde, which is further reduced to ethanol, using re-engineered metabolic routes. WO2010/104938 is incorporated herein by reference.

In some embodiments, electrochemically generated, external reducing equivalents can be provided by the EBM disclosed herein to the redox enzymes in the second engineered metabolic pathway, such as FLD. The reducing equivalents can be provided via one or more electron transfer mediators such as Neutral Red, Methylene Blue, Methyl Viologen, quinone, NAD+ and/or NADP+.

Figure 4:
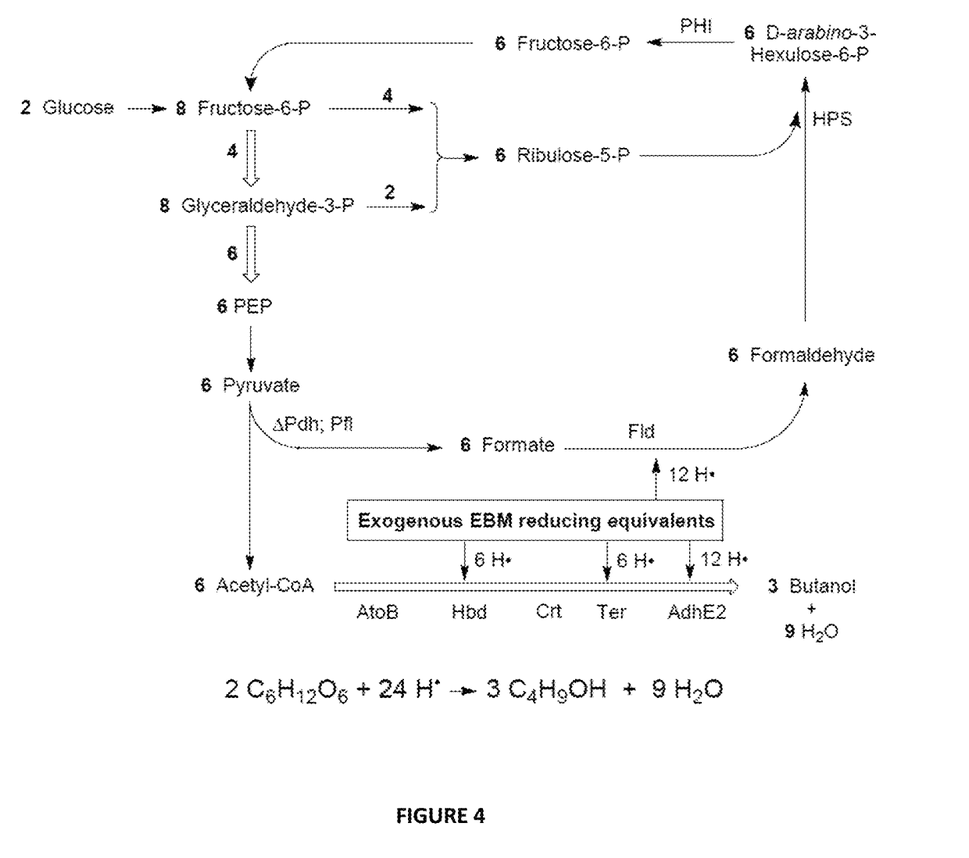
FIG. 4 illustrates an embodiment of a first and second engineered pathway. The reducing equivalents required for both the first engineered butanol pathway and the formaldehyde dehydrogenase in the second engineered pathway can be provided electrochemically by the EBM.

FIG. 4 illustrates an embodiment of the present disclosure wherein the first and second engineered pathways are provided, e.g., optionally in an engineered host cell. The host cell can be a bacterium (e.g., *E. coli* or *Clostridium acetylbutylicum*) or fungus. The bold numbers indicate molar equivalents of each compound in the pathway, and the molar flux between metabolic steps. In FIG. 4:

First Engineered Pathway

AtoB=acetyl-CoA acetyltransferase (EC 2.3.1.9);
Hbd=3-hydroxybutyryl-CoA dehydrogenase (EC 1.1.1.157);
Crt=3-hydroxybutyryl-CoA dehydratase (EC 4.2.1.5);
Ter=trans-enoyl-CoA reductase (EC 1.3.1.38);
AdhE2=aldehyde/alcohol dehydrogenase (EC 1.2.157/EC 1.1.1.1)

Second Engineered Pathway

ΔPdh=deletion of pyruvate dehydrogenase activity (EC 1.2.4.1)
Pfl=pyruvate:formate lyase (EC 2.3.1.54);
Fld=formaldehyde dehydrogenase (EC 1.2.1.46);
HPS=3-hexulose-6-phosphate synthase (EC 4.1.2.43);
PHI=6-phospho-3-hexuloisomerase (EC 5.3.1.27)

The first engineered pathway is for the production of 1-butanol from acetyl-CoA using the enzymes AtoB, Hdb, Crt, Ter and AdhE2. The second engineered pathway replaces pyruvate dehydrogenase with pyruvate:formate lyase (Pfl) and uses the three enzymes formaldehyde dehydrogenase (Fld), 3-hexulose-6-phosphate synthase (HPS) and 6-phospho-3-hexuloisomerase (PHI) to direct the formate from the pyruvate:formate lyase through the RuMP pathway where it is recovered as fructose-6-phosphate, and the carbon re-enters the glycolytic pathway. The reducing equivalents required for both the first engineered butanol pathway and the formaldehyde dehydrogenase in the second engineered pathway can be provided electrochemically by the EBM disclosed herein.

In some embodiments, within the host cell, a first engineered pathway for production of 1-butanol from acetyl-CoA can be expressed. This first engineered pathway comprises the enzymes acetyl-CoA acetyltransferase (AtoB, EC 2.3.1.9), 3-hydroxybutyryl-CoA dehydrogenase (Hbd, EC 1.1.1.157), 3-hydroxybutyryl-CoA dehydratase (Crt, EC 4.2.1.5), trans-enoyl-CoA reductase (Ter, EC 1.3.1.38) and aldehyde/alcohol dehydrogenase (AdhE2, EC 1.2.157/EC 1.1.1.1).

The host cell further contains a second engineered pathway for the reduction of formate to formaldehyde and the ultimate recovery of the formaldehyde as fructose-6-phosphate. This second engineered pathway comprises the enzymes pyruvate:formate lyase (Pfl, EC 2.3.1.54), formaldehyde dehydrogenase (Fld, EC 1.2.1.46), hexulose-6-phosphate synthase (HPS, EC 4.1.2.43), and 6-phospho-3-hexuloisomerase (HPI, EC 5.3.1.27). In order for the second engineered pathway to be of use, the pyruvate dehydrogenase (Pdh, EC 1.2.4.1) of the cell has been disabled, deleted or otherwise rendered non-functional in order to prevent the loss of carbon as $CO_2$ at the end of the glycolytic pathway.

In certain embodiments, the host cell has the enzymes that would otherwise catalyze the production of succinic acid from phosphoenyl pyruvate (fumarate reductase, FrdBC, EC 1.3.1.6) the formation of lactate from pyruvate (lactate dehydrogenase, Ldh, EC 1.1.1.27), ethanol from acetyl-CoA (acetaldehyde dehydrogenase, AdhE, EC 1.2.1.10) or acetate from acetyl-CoA (acetyl-CoA-phosphate acetyltransferase, Pta, EC 2.3.1.8) disabled, deleted or otherwise rendered non-functional.

In various embodiments, the host cell containing the metabolic engineered pathways described herein receives electrochemically generated reducing equivalents from the EBM either directly or via an optional electron transport mediator such as Neutral Red.

In some embodiments, the cathode chamber of the EBM continuously receives a process stream containing the appropriate host cell in which the first and second engineered pathways have been expressed. The process stream can be a fermentation broth for culturing the host cell. The host cell can a bacterium or a fungus, such as *E. coli, Actinobacillus succinogenes, Bacillus subtilis, Clostridium acetylbutylicum* or another *Clostridium* species, *Saccharomyces cerevisiae*, the Cargill CB1 yeast, a *Pichia* species or an *Aspergillus* species.

Under working conditions, glucose enters the host cell and proceeds though glycolysis to produce pyruvate. The produced pyruvate is cleaved by pyruvate:formate lyase to yield acetyl-CoA and formate. The acetyl-CoA proceeds through the first engineered pathway to produce 1-butanol, with the enzymes Hbd (3-hydroxybutyryl-CoA dehydrogenase), Ter (trans-enoyl-CoA reductase) and AdhE2 (aldehyde/alcohol dehydrogenase) receiving exogenous reducing equivalents generated by the EBM. The formate produced from the pyruvate is reduced by Fld (formaldehyde dehydrogenase) also using reducing equivalents generated by the EBM. The formaldehyde is condensed via HPS (3-hexulose-6-phosphate synthase) with ribulose-5-phosphate provided by the pentose pathways naturally present in the host cell to produce D-arabino-3-Hexulose-6-phosphate. This is isomerized via HPI (6-phospho-3-hexuloisomerase) to fructose-6-phosphate which re-enters the glycolytic pathway. In this manner, all carbon entering the overall system as glucose is transformed to 1-butanol.

It will be clear that in the present disclosure, $CO_2$ is not generated during the formation of 1-butanol and the concomitant issues of recovering $CO_2$ for use in desired metabolic pathways is avoided. This allows achievement of 100% carbon efficiency.

It will also be clear that in the present disclosure that the electricity input of this EBM system may come from a renewable resource (wind, solar, hydroelectric etc.).

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Equivalents

The present disclosure provides among other things novel methods and devices for providing reducing equivalents to biological systems. While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

INCORPORATION BY REFERENCE

All publications, patents and patent applications cited above are incorporated by reference herein in their entirety for all purposes to the same extent as if each individual publication or patent application were specifically indicated to be so incorporated by reference.

What is claimed is:

1. A system for 1-butanol production, comprising:
an electrochemical bioreactor module for providing reducing equivalents;
an engineered cell for receiving and using the reducing equivalents to produce 1-butanol, wherein the engineered cell comprises four exogenously introduced enzymes that are pyruvate:formate lyase (Pfl, EC 2.3.1.54), formaldehyde dehydrogenase (Fld, EC 1.2.1.46), hexulose-6-phosphate synthase (HPS, EC 4.1.2.43), and 6-phospho-3-hexuloisomerase (HPI, EC 5.3.1.27), and wherein in the engineered cell the endogenous pyruvate dehydrogenase (Pdh, EC 1.2.4.1) has been disabled, deleted or otherwise rendered non-functional;
wherein the four exogenously introduced enzymes convert pyruvate into formate without producing $CO_2$, and convert the formate to fructose-6-phosphate;
wherein the engineered cell is selected from a bacterium or a fungus.

2. The system of claim 1 wherein the engineered cell further comprises exogenously introduced acetyl-CoA acetyltransferase (AtoB, EC 2.3.1.9), 3-hydroxybutyryl-CoA dehydrogenase (Hbd, EC 1.1.1.157), 3-hydroxybutyryl-CoA dehydratase (Crt, EC 4.2.1.5), trans-enoyl-CoA reductase (Ter, EC 1.3.1.38) and aldehyde/alcohol dehydrogenase (AdhE2, EC 1.2.157/EC 1.1.1.1).

3. The system of claim 1 wherein in the engineered cell, the endogenous fumarate reductase (FrdBC, EC 1.3.1.6), lactate dehydrogenase (Ldh, EC 1.1.1.27), acetaldehyde dehydrogenase (AdhE, EC 1.2.1.10) and/or acetyl-CoA-phosphate acetyltransferase (Pta, EC 2.3.1.8) have been disabled, deleted or otherwise rendered non-functional.

4. The system of claim 1 wherein the reducing equivalents are transported by an electron transfer mediator (ETM).

5. The system of claim 4 wherein the ETM is selected from one or more of Neutral Red, Methylene Blue, Methyl Viologen, quinone, NAD+ and NADP+.

6. The system of claim 1 wherein the bacterium is selected from *E. coli, Bacillus subtilis, Clostridium* acetylbutylicum or another *Clostridium* species.

7. The system of claim 1 wherein the fungus is selected from *Saccharomyces cerevisiae*, a *Pichia* species or an *Aspergillus* species.

8. A method for producing 1-butanol, comprising providing the system of claim 1 in the presence of a carbon source.

9. The method of claim 8, wherein the carbon source is glucose.

10. The method of claim 8 wherein the engineered cell further comprises exogenously introduced acetyl-CoA acetyltransferase (AtoB, EC 2.3.1.9), 3-hydroxybutyryl-CoA dehydrogenase (Hbd, EC 1.1.1.157), 3-hydroxybutyryl-CoA dehydratase (Crt, EC 4.2.1.5), trans-enoyl-CoA reductase (Ter, EC 1.3.1.38) and aldehyde/alcohol dehydrogenase (AdhE2, EC 1.2.157/EC 1.1.1.1).

11. The method of claim 8 wherein in the engineered cell, the endogenous fumarate reductase (FrdBC, EC 1.3.1.6), lactate dehydrogenase (Ldh, EC 1.1.1.27), acetaldehyde dehydrogenase (AdhE, EC 1.2.1.10) and/or acetyl-CoA-phosphate acetyltransferase (Pta, EC 2.3.1.8) have been disabled, deleted or otherwise rendered non-functional.

12. The method of claim 8 wherein the reducing equivalents are transported by an electron transfer mediator (ETM).

13. The method of claim 12 wherein the ETM is selected from one or more of Neutral Red, Methylene Blue, Methyl Viologen, quinone, NAD+ and NADP+.

14. The method of claim 8 wherein the bacterium is selected from *E. coli, Bacillus subtilis, Clostridium* acetylbutylicum or another *Clostridium* species.

15. The method of claim 8 wherein the fungus is selected from *Saccharomyces cerevisiae*, a *Pichia* species or an *Aspergillus* species.

* * * * *